US012626418B2

(12) United States Patent
Park

(10) Patent No.: US 12,626,418 B2
(45) Date of Patent: *May 12, 2026

(54) DEVICE AND METHOD FOR SUPPORTING BIOMETRIC IMAGE FINDING/DIAGNOSIS

(71) Applicant: XAIMED CO., LTD, Seoul (KR)

(72) Inventor: Sang Min Park, Seoul (KR)

(73) Assignee: XAIMED CO., LTD, Seoul (KR)

( * ) Notice: Subject to any disclaimer, the term of this patent is extended or adjusted under 35 U.S.C. 154(b) by 336 days.

This patent is subject to a terminal disclaimer.

(21) Appl. No.: 18/282,544

(22) PCT Filed: Dec. 20, 2021

(86) PCT No.: PCT/KR2021/019356
§ 371 (c)(1),
(2) Date: Sep. 18, 2023

(87) PCT Pub. No.: WO2022/158727
PCT Pub. Date: Jul. 28, 2022

(65) Prior Publication Data
US 2025/0111697 A1     Apr. 3, 2025

(30) Foreign Application Priority Data

Jan. 25, 2021     (KR) ........................ 10-2021-0009964

(51) Int. Cl.
*G16H 30/40*        (2018.01)
*A61B 3/12*        (2006.01)
(Continued)

(52) U.S. Cl.
CPC ................ *G06T 11/00* (2013.01); *A61B 3/12* (2013.01); *A61B 3/14* (2013.01); *G06T 3/40* (2013.01);
(Continued)

(58) Field of Classification Search
CPC .... A61B 3/12; A61B 3/14; A61B 3/00; A61B 3/0025; G06T 3/40; G06T 2207/20084;
(Continued)

(56) References Cited

U.S. PATENT DOCUMENTS

| | | | | |
|---|---|---|---|---|
| 10,111,582 B2 * | 10/2018 | Nakagawa | ............ | G06T 7/0012 |
| 2016/0292856 A1 * | 10/2016 | Niemeijer | ............ | G06T 7/0012 |
| 2019/0108917 A1 * | 4/2019 | Suehling | ................ | G16H 10/60 |

FOREIGN PATENT DOCUMENTS

| | | | | |
|---|---|---|---|---|
| EP | 3745309 A1 * | 12/2020 | .......... | G06F 18/214 |
| JP | 2017-077414 A | 4/2017 | | |

(Continued)

OTHER PUBLICATIONS

Iqbal, Talha, and Hazrat Ali. "Generative Adversarial Network for Medical Images (Mi-Gan)—Journal of Medical Systems." SpringerLink, Springer US, Oct. 12, 2018, link.springer.com/article/10.1007/s10916-018-1072-9. (Year: 2018).*

(Continued)

*Primary Examiner* — Amandeep Saini
*Assistant Examiner* — Jaspreet Kaur
(74) *Attorney, Agent, or Firm* — Han's Law Office

(57)     ABSTRACT

Provided are a device, a method, and a system for supporting biometric image finding/diagnosis, the device comprising: a processor; and a memory including one or more instructions implemented to be executed by the processor, wherein the processor; extracts a first attribute information from a first biometric image of an object on the basis of a machine learning model; changes the first attribute information of the first biometric imaged by mapping adversarial noise to the first biometric image, so as to generate a second biometric image having second attribute information; and displays the first biometric image having the first attribute information (Continued)

and the second biometric image having the second attribute information on a display unit.

13 Claims, 12 Drawing Sheets

(51) Int. Cl.

| | |
|---|---|
| *A61B 3/14* | (2006.01) |
| *G06T 3/40* | (2006.01) |
| *G06T 11/00* | (2006.01) |
| *G06V 10/56* | (2022.01) |
| *G06V 40/18* | (2022.01) |
| *G16H 30/20* | (2018.01) |

(52) U.S. Cl.
CPC ............ *G06V 10/56* (2022.01); *G06V 40/193* (2022.01); *G16H 30/20* (2018.01); *G16H 30/40* (2018.01)

(58) Field of Classification Search
CPC .......... G06T 2207/30041; G06V 10/56; G06V 40/193; G16H 30/40; G16H 50/20; G06N 3/08; G06N 20/00; G06N 3/0464
See application file for complete search history.

(56) References Cited

FOREIGN PATENT DOCUMENTS

| | | | |
|---|---|---|---|
| JP | 2020120704 A | * | 8/2020 |
| KR | 10-1848321 B1 | | 4/2018 |
| KR | 10-2019-0087272 A | | 7/2019 |
| KR | 10-2020-0005407 A | | 1/2020 |
| KR | 10-2021-0096737 A | | 8/2021 |

OTHER PUBLICATIONS

Jooyoung Chang, MD et al.; Explaining the Rationale of Deep Learning Glaucoma Decisions with Adversarial Examples; Jun. 26, 2020; American Academy of Ophthalmology(2020), ISSN 0161-6420/20.

* cited by examiner

55

53

75

75a

73

73a

71

71a

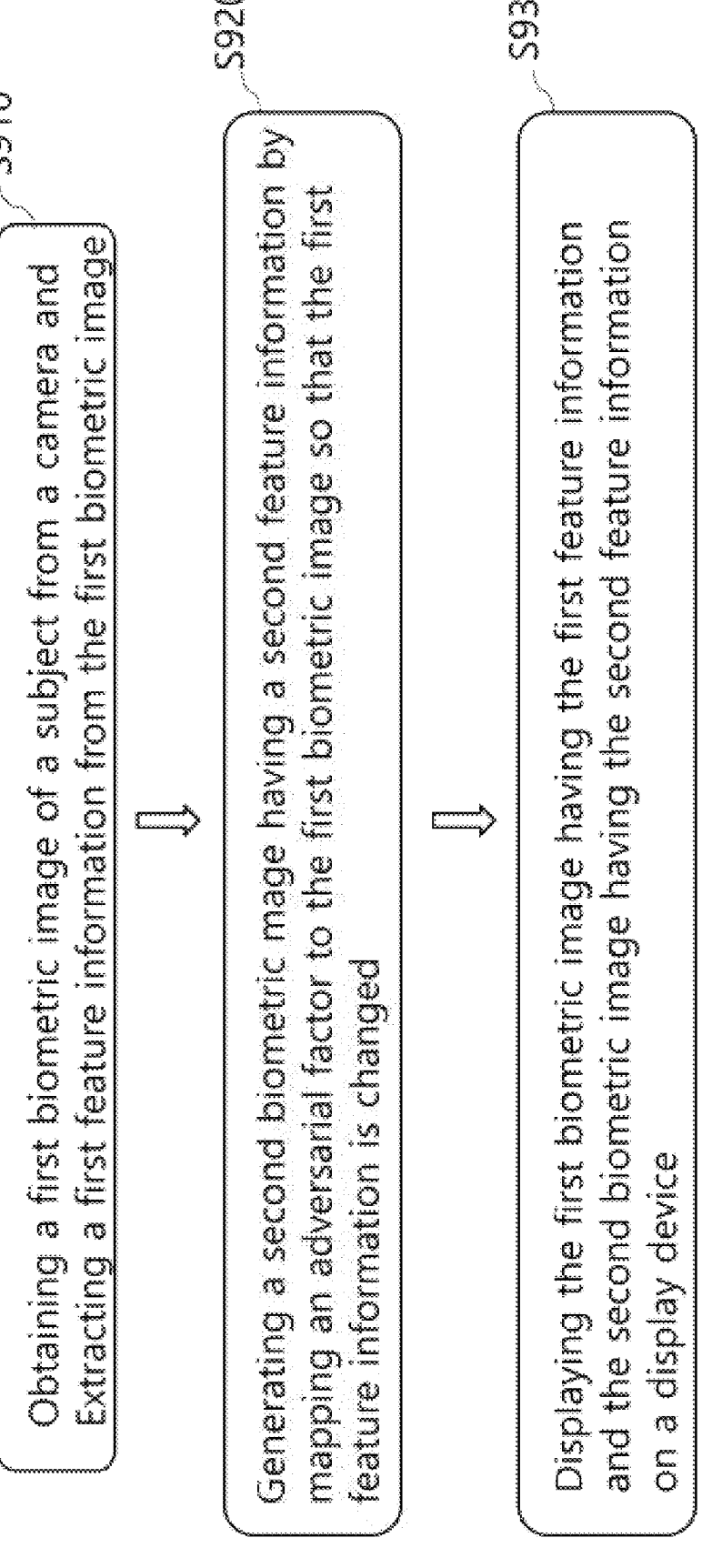

S910

Obtaining a first biometric image of a subject from a camera and Extracting a first feature information from the first biometric image

S920

Generating a second biometric image having a second feature information by mapping an adversarial factor to the first biometric image so that the first feature information is changed

S930

Displaying the first biometric image having the first feature information and the second biometric image having the second feature information on a display device

FIG. 10

DEVICE AND METHOD FOR SUPPORTING BIOMETRIC IMAGE FINDING/DIAGNOSIS

TECHNICAL FIELD

The present disclosure relates to diagnosing disease of biometric images, more particularly, to an apparatus and method for supporting reading of biometric images using a machine learning model.

BACKGROUND ART

With development of artificial intelligence learning models, many machine learning models are being used to read medical images. For example, the machine learning models such as Convolutional Neural Networks (CNN), Deep Neural Networks (DNN), Recurrent Neural Networks (RNN), and Deep Belief Networks (DBN) are being applied to detect, classify, and characterize the medical images.

The machine learning models are currently being used to support an image reading, an image finding, an image diagnosis to predict a disease of a patient. More specifically, a method of supporting the image reading, the image finding, and the image diagnosis of the medical image is to obtain the biometric image from the patient, extract feature from the fundus image based on the machined learning models, provide the feature to a practitioner, and predict the patient's disease based on it. In this case, the feature includes various information for the medical image.

However, even if the feature of the medical image is extracted based on the machine learning model, if the learning information input to the machine learning model is inadequate or insufficient for various factors such as a lack of learning data input to the machine learning mode, differences in environments of medical imaging (e.g., a health check-up center, a private ophthalmology clinic, a general hospital, etc.), a difference of learning data (e.g., only a fundus image of a normal person, only a fundus image of an abnormal person), a difference of an imaging apparatuses, an entity such as a medical practitioner can receive incorrect information from the machined learning model. For example, differences in learning information are the lack of learning data input to the learning model, differences in imaging environments (e.g., health examination centers, private ophthalmology hospitals, general ophthalmology hospitals), and groups (e.g., only normal people, only abnormalities). It may be a difference between a person, a normal person and an abnormal person), a difference between an imaging device, and the like. These various factors can lead to erroneous prediction of the patient's disease.

Thus, even though the learning information is poor, there is a need for systems and methods that can do the more accurate prediction of the patient's disease using the learning information image and can explain why such the patient's disease was predicted.

DESCRIPTION OF EMBODIMENTS

Technical Problem

An embodiment of the present disclosure is to provide an apparatus for supporting reading of a biometric image capable of improving the accuracy and reliability of biometric image reading based on a machine learning model.

Another embodiment of the present disclosure is to provide an apparatus for supporting reading of a biometric image capable of explaining the reason for biometric image reading.

Solution to Problem

In one aspect of the present disclosure, an apparatus for supporting reading of a biometric of a subject includes a processor and a memory including one or more sequences of instructions which, when executed by the processor, causes steps to be performed comprising: extracting a first feature information from a first biometric image of the subject based on a machine learning model; generating a second fundus image having a second feature information by mapping an adversarial noise to the first biometric image so that the first feature information of the first biometric image is changed; and displaying the first biometric image having the first feature information and the second biometric image having the second feature information on a display device.

Desirably, the steps further may include generating images in which a specific area of each of the first biometric image and the second biometric image is enlarged; and displaying the images on the display device.

Desirably, the steps further may include generating a third biometric image in which an adversarial noise is visualized, by filtering the second biometric image mapped by the adversarial noise therein; and displaying the third biometric image on the display device.

Desirably, the steps further may include generating a pre-biometric image by pre-processing the first biometric image to enlarge or partially partition a specific area of the first biometric image.

In another aspect of the present disclosure, a method for supporting reading of a biometric image of a subject includes extracting a first feature information from a first biometric image of the subject based on a machine learning model; generating a second biometric image having a second feature information by mapping an adversarial noise to the first biometric image so that the first feature information of the first biometric image is changed; and displaying the first biometric image having the first feature information and the second biometric image having the second feature information on a display device.

Advantageous Effects of Disclosure

According to the present disclosure, the apparatus for supporting reading of a biometric image can improve accuracy and reliability in reading the biometric image based on a machine learning model.

Moreover, even if the training data for the machine learning model is small, the apparatus according to the present disclosure can more accurately and reliably read the biometric image by generating and comparing comparable biometric images.

BRIEF DESCRIPTION OF DRAWINGS

FIG. 10 shows a flowchart illustrating an exemplary process for supporting reading of a biometric image by a processor according to embodiments of the present disclosure.

DETAILED DESCRIPTION

Figure 1:
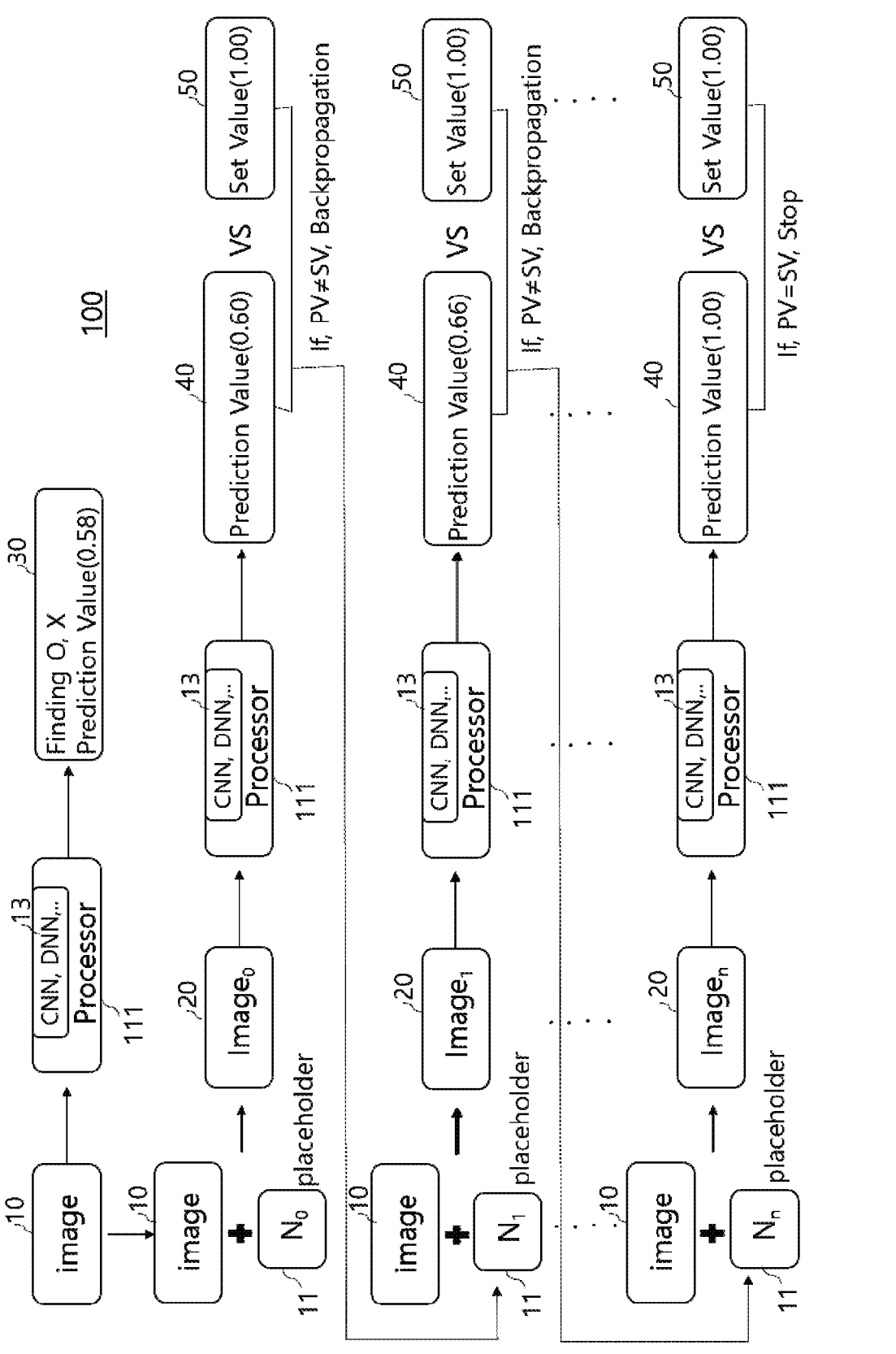
FIG. 1 shows a flowchart of an illustrative process for generating a feature information of a biometric image according to embodiments of the present disclosure.

In the following description, for purposes of explanation, specific details are set forth in order to provide an understanding of the disclosure. It will be apparent, however, to one skilled in the art that the disclosure can be practiced without these details.

Furthermore, one skilled in the art will recognize that embodiments of the present disclosure, described below, may be implemented in a variety of ways, such as a process, an apparatus, a system, a device, or a method on a tangible computer-readable medium.

The terms "comprise/include" used throughout the description and the claims and modifications thereof are not intended to exclude other technical features, additions, components, or operations.

In the following description, it shall also be noted that the terms "learning" shall be understood not to intend mental action such as human educational activity because of referring to performing machine learning by a processing module such as a processor, a CPU, an application processor, micro-controller, so on.

An "image" is defined as a reproduction or imitation of the form of a person or thing, or specific characteristics thereof, in digital form. An image can be, but is not limited to, a JPEG image, a PNG image, a GIF image, a TIFF image, or any other digital image format known in the art. "Image" is used interchangeably with "photograph".

A "feature(s)" is defined as a group of one or more descriptive characteristics of subjects that can discriminate for disease. A feature can be a numeric attribute.

The embodiments described herein relate generally to diagnostic medical images. Although any type of medical image can be used, these embodiments will be illustrated in conjunction with fundus images and bond joint images. However, the disclosed methods, systems, apparatuses, and devices can also be used with medical images of other ocular structures, or any other biological tissues image of which can support the diagnosis of a disease condition. Furthermore, the methods disclose herein can be used with a variety of imaging modalities including but not limited to: computed tomography (CT), magnetic resonance imaging (MRI), computed radiography, magnetic resonance, angioscopy, optical coherence tomography, color flow Doppler, cystoscopy, diaphanography, echocardiography, fluoresosin angiography, laparoscopy, magnetic resonance angiography, positron emission tomography, single photon emission computed tomography, x-ray angiography, nuclear medicine, biomagnetic imaging, culposcopy, duplex Doppler, digital microscopy, endoscopy, fundoscopy, laser, surface scan, magnetic resonance spectroscopy, radio graphic imaging, thermography, and radio fluroscopy.

Components shown in diagrams are illustrative of exemplary embodiments of the disclosure and are meant to avoid obscuring the disclosure. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components that may be implemented in software, hardware, or a combination thereof. Furthermore, one skilled in the art shall recognize that certain steps may optionally be performed that steps may not be limited to the specific order set forth herein, and that certain steps may be performed in different orders, including being done contemporaneously. Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," or "in embodiments" in various places in the specification are not necessarily all referring to the same embodiment or embodiments. Unless the context clearly indicates otherwise, the singular forms "a," "an," and "the" are intended to include the plural forms as well. Also, when description related to a known configuration or function is deemed to render the present disclosure ambiguous, the corresponding description is omitted.

FIG. 1 shows a flowchart of an illustrative process for generating a feature information of a biometric image by an apparatus according to embodiments of the present disclosure.

In general, when a biometric image such as a fundus image is acquired from an arbitrary subject (e.g., a patient), a feature information is derived from the biometric image using a machine learning model. However, the feature information of such the biometric image may not derive reliable feature information due to the difference in learning data input to the machine learning model. In addition, even if the feature information of the biometric image is primarily derived, support for reliable reading and diagnosis of the biometric image may not be provided due to a lack of explanations that can be supported in predicting and diagnosing any diseases based on the feature information of the biometric image.

To solve such unreliable biometric image reading, the present apparatus can automatically generate the feature information of the biometric image that has reliability and can support the medical practitioner to accurately read the derived biometric image. That is, the apparatus according to embodiments of the present disclosure can firstly find the feature information from the biometric image captured by a camera or the like on the biological tissue of the subject, and secondarily help to determine or explain whether the biometric image of the subject including the feature information is actually a reliable biometric image.

In order to generate the feature information of the biometric image, the apparatus 100 may extract a first feature information 30 from a first biometric image 10 that is photographed by imaging means such as a camera, using a machine learning model 13 (e.g., CNN, DNN, etc.). The extracted first feature information 30 may be stored in a memory unit 113 or a storage device 115 described below. In embodiments, the machine learning model 13 may be installed into a processor 111 and executed by the processor 111. The machine learning model 13 may be installed into a computer-readable medium or media (not shown in FIG. 1) and executed by the computer-readable medium or media. In alternative embodiments, the machine learning model 13 may be installed into the memory unit 113 or the storage device 115 and executed by the processor 111.

In addition, the processor 111 may store clinical information of a subject (e.g., a patient) in the memory unit 113 or the storage device 115 in advance. In embodiments, the processor 111 may extract the first feature information of the first biometric image 10 based on the machine learning model 13 by using the clinical information of the subject stored in the memory unit 113 or the storage device 115. In embodiments, the clinical information may be, but is not limited to, the age, sex, medical history, questionnaire information, test measurement values, exercise habits, eating habits, family history related to the medical history, alcohol consumption, smoking status. In embodiments, the questionnaire information may include neuromedical questionnaire that a practitioner (e.g., a medical doctor) can perform on the subject or may mean ideal findings currently observed to the subject, unlike medical history thereof. In embodiments, the test measurement values may include an intraocular pressure, a blood pressure, a blood sugar level, and the like.

The first feature information 30 may be various information that it can support an entity (e.g., a practitioner or a computing device) reading a biometric image such as predicting or diagnosing disease. For instance, if the first biometric image is a fundus image, when predicting or diagnosing glaucoma in the fundus image of the subject, the first feature information of the fundus image may include at least one of various information such as the increased C/D ratio (Cup-to-Disk ratio) information, thickness change information for Disc Rim Thinning, contrast information for Retinal Nerve Fiber Layer Defect, or location information of Retinal Hemorrhage included in the fundus image. For another instance, when predicting or diagnosing diabetic retinopathy in the fundus image of the subject, the first feature information may include at least one of location information on Drusen, information on Retinal Pigment Epithelium Change, information on Chorioretinal Scar/Atrophy, information on Peripapillary Atrophy, information on Hard Exudate, information on Cotton-Wool Patch, information on Hemorrhage, information on Vascular Abnormality, information on Laser Scar, information on Subretinal Fluid, information on Myelinated Nerve Fiber, and information on Epiretinal Membrane included in the fundus image. In addition, the first feature information may include at least one of optic nerve vascular information that provides information on major organs of the eyeball, binocular classification information indicating whether the fundus image is an image of the left eye or the right eye, location information indicating a location of at least one of the macular and optic disk, and partitioning information indicating a segment of the fundus image and the like in the fundus image.

Moreover, if the first biometric image is a bone joint image, when predicting or diagnosing a joint condition in the bone joint image of the subject, the first feature information of the bone joint image may include information about joint space narrowing, osteophyte, sclerosis, bone end deformity included in the bone joint image.

In this case, in embodiments, on the results performed by the processor 111, the apparatus 100 may appear the finding (Finding O, X) indicating the presence or absence of a disease in the first biometric image on the basis of the first feature information, or a prediction value indicating the presence or absence of the finding on a display device 130, 330 describe below. In embodiments, the prediction value may be expressed as a percentage or a number between 0 and 1, an explanation of presence or absence of the finding and the prediction value will be described in more detail below.

Meanwhile, in embodiments, the processor 111 may generate a second biometric image 20, that is another image artificially made similar to the first biometric image 10 using a GAN (Generative Adversarial Networks) learning model.

In preferred embodiments, the processor 111 may generate a second biometric image 20 that is made using a photographed original image (i.e., the first biometric image 10). The photographed original image can more accurately reflect its own feature information rather than another image artificially made similar to the first biometric image 10 using a GAN (Generative Adversarial Networks) learning model. Therefore, the feature information of the second biometric image 20 that is made using a photographed original image may have better reliability. More specifically, the processor 111 may map an adversarial factor 11 into the first biometric image 10. By doing so, the first feature information 30 of the first biometric image 10 is changed so that it may generate the second biometric image 20 including a second feature information 40. In embodiments, the generated second biometric image 20 including the second feature information 40 may be stored in the memory unit 113 or the storage device 115 described below.

In embodiments, the adversarial factor 11 may be adversarial noise (N0, ., ., ., Nn) that is attacked to the first biometric image 10. For example, the adversarial noise may include at least one of a value that adjusts the gradation level of the R, G, and B pixels representing the first biometric image 10, a value that adjusts the color of the R, G, and B pixels of the first biometric image 10, a value that locally adjusts the contrast ratio in the first biometric image 10. It should be noted that the adversarial factor 11 may include any factor that can change the first feature information of the first biometric image 10.

In embodiments, the second biometric image 20 including the second feature information 40 may be generated by mapping the adversarial factor 11 to the first biometric image 10 once. In alternative embodiments, the second biometric image 20 including the second feature information 40 may be generated by repeatedly mapping the adversarial factor 11 to the first biometric image 10 so that the prediction value for the second feature information 40 obtained based on the machine learning model 13 converges to a set value 50.

For instance, if the set value is 1 and the prediction value of the first biometric image 10 obtained based on the machine learning model 13 is 0.58, the adversarial factor 11 is mapped to the first biometric image 10 by the processor 111, thereby being generated by the second biometric image 20, and then, the first biometric image 10 may be repeatedly mapped by the adversarial factor 11 so that the prediction values (0.60, 0.66, 0.68, . . . ) of the generated second biometric image 20 obtained based on the machine learning model 13 converges to the set value 1.

For another instance, if the set value is 0 and the prediction value of the first biometric image obtained based on the machine learning model 13 is 0.58, the first biometric image 10 is mapped by the adversarial factor 11, thereby being generated by the second biometric image 20, and then, the first biometric image 10 may be repeatedly mapped by the adversarial factor 11 so that the prediction values (0.56, 0.54, 0.52, . . . ) of the generated second biometric image 20 obtained based on the machine learning model 13 converges to the set value 0. Thus, the number of second biometric images 20 may be determined according to the number of set values.

If the set value is 1, it may mean that the generated biometric image (the second biometric image 20) is a biometric image that is close to an abnormal biometric image in which any disease can be predicted or diagnosed thereon. In such case, it may mean that there is the finding. if the set value is 0, it may mean that the generated biometric image (the second biometric image 20) is a biometric image that is close to a normal biometric image in which any disease cannot be predicted or diagnosed thereon. In such case, it may mean that there is no the finding.

In embodiments, the first biometric image 10 having the first feature information 30 obtained based on the machine learning model 13 and the second biometric image 20 having the second feature information 40 obtained by mapping the adversarial factor 11 may be provided to at least one of a practitioner (e.g., a medical doctor) through a transmission module such as a display adapter 119 or a network adapter 118, one and more remote computing devices 200, 300, 400 that is linked to the computing device 110 through an Internet network, and the other device that can use the biometric image 10 and the second biometric image 20, described below.

In embodiments, since the second biometric image 20 with the second feature information 40 is a biometric image close to the normal or abnormal biometric image, when the entity (e.g., the practitioner, the remote computing device) reads the first biometric image 10, the apparatus 100 may allow the entity to read the first biometric image 10 by comparing it with the second biometric image 20, so that the entity can easily and accurately read the first biometric image 10. In addition, since the processor 111 may generate a comparison image (i.e., the second biometric image 20) for the first biometric image 10, and compare the comparison image with the first biometric image 10, it is possible to convincingly explain the reason why such a reading result is obtained for the first biometric image 10. Accordingly, the reliability of the reading of the first biometric image 10 having the first feature information 30 can be improved.

In addition, in embodiments, the apparatus 100 may display a difference between the first feature information 30 of the first biometric image 10 and the second feature information 40 of the second biometric image 20 on the display device 130 described below and may provide the difference to the entity.

Figure 2:
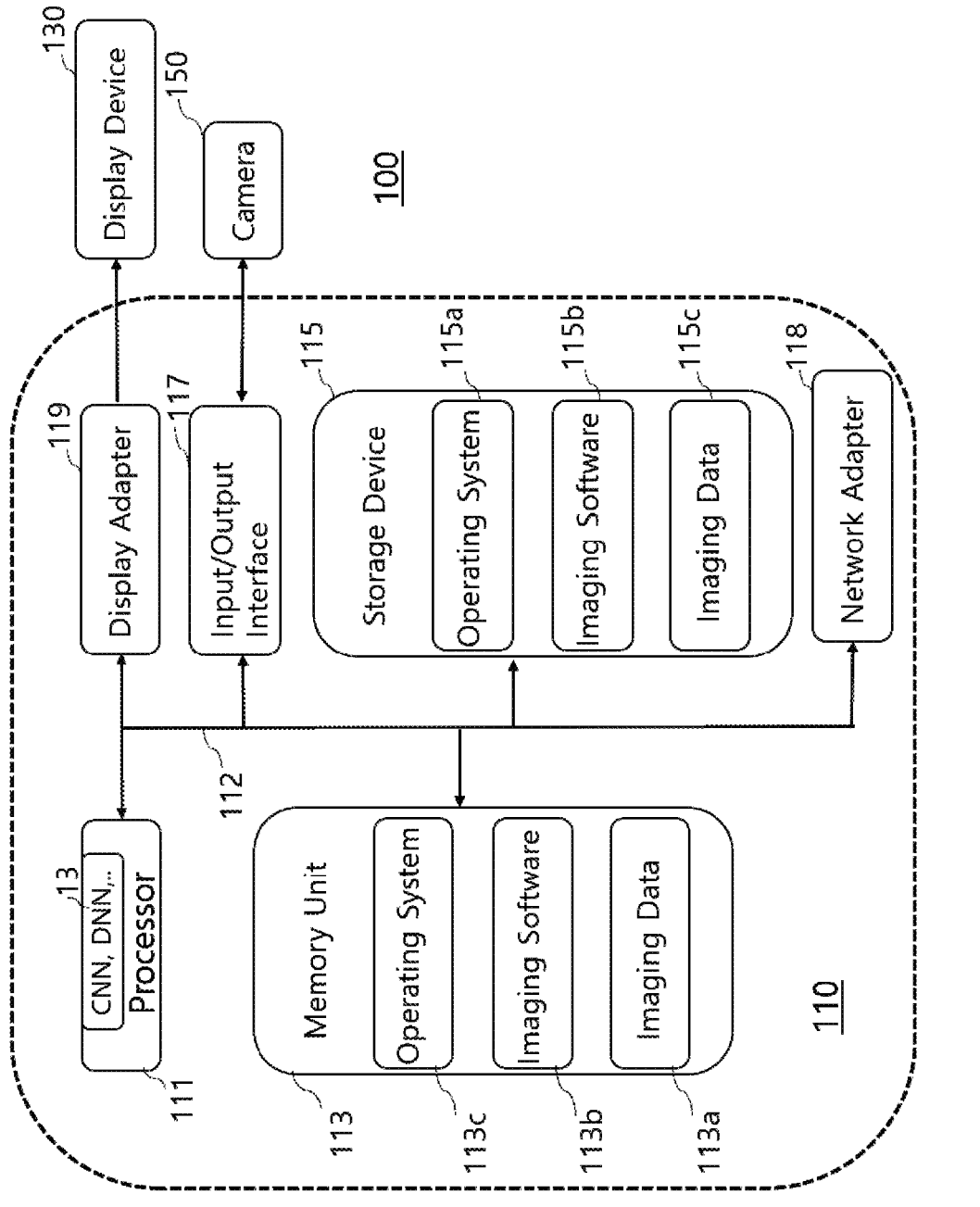
FIG. 2 shows a schematic diagram of an illustrative apparatus for supporting reading of a biometric image according to embodiments of the present disclosure.

FIG. 2 is a schematic diagram of an illustrative apparatus 100 for supporting reading of a biometric image according to embodiments of the present disclosure.

As depicted, the apparatus 100 may include a computing device 110, a display device 130 and a camera 150. In embodiments, the computing device 110 may include, but is not limited thereto, one or more processor 111, a memory unit 113, a storage device 115, an input/output interface 117, a network adapter 118, a display adapter 119, and a system bus 112 connecting various system components to the memory unit 113. In embodiments, the apparatus 100 may further include communication mechanisms as well as the system bus 112 for transferring information.

In embodiments, the communication mechanisms or the system bus 112 may interconnect the processor 111, a computer-readable medium, a short range communication module (e.g., a Bluetooth, a NFC), the network adapter 118 including a network interface or mobile communication module, the display device 130 (e.g., a CRT, a LCD, etc.), an input device (e.g., a keyboard, a keypad, a virtual keyboard, a mouse, a trackball, a stylus, a touch sensing means, etc.) and/or subsystems.

In embodiments, the processor 111 is, but is not limited to, a processing module, a Computer Processing Unit (CPU), an Application Processor (AP), a microcontroller, a digital signal processor.

In embodiments, the processor 111 may include an image filter such as a high pass filter or a low pass filter to filter a specific factor in a biometric image. In addition, the processor 111 may communicate with a hardware controller such as the display adapter 119 to display a user interface on the display device 130.

In embodiments, the processor 111 may access the memory unit 113 and execute commands stored in the memory unit 113 or one or more sequences of instructions to control the operation of the apparatus 100.

The commands or sequences of instructions may be read in the memory unit 113 from computer-readable medium or media such as a static storage or a disk drive but is not limited thereto. In alternative embodiments, a hard-wired circuitry which is equipped with a hardware in combination with software commands may be used. The hard-wired circuitry can replace the soft commands. The instructions may be an arbitrary medium for providing the commands to the processor 111 and may be loaded into the memory unit 113.

In embodiments, the system bus 112 may represent one or more of several possible types of bus structures, including a memory bus or memory controller, a peripheral bus, an accelerated graphics port, and a processor or local bus using any of a variety of bus architectures. For instance, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like.

In embodiments, the system bus 112, and all buses specified in this description can also be implemented over a wired or wireless network connection.

A transmission media including wires of the system bus 112 may include at least one of coaxial cables, copper wires, and optical fibers. For instance, the transmission media may take a form of sound waves or light waves generated during radio wave communication or infrared data communication.

In embodiments, the apparatus 100 may transmit or receive the commands including messages, data, and one or more programs, i.e., a program code, through a network link or the network adapter 118.

In embodiments, the network adapter 118 may include a separate or integrated antenna for enabling transmission and reception through the network link. The network adapter 118 may access a network and communicate with a remote computing devices 200, 300, 400 in FIG. 3.

In embodiments, the network may be, but is not limited to, at least one of LAN, WLAN, PSTN, and cellular phone networks. The network adapter 118 may include at least one of a network interface and a mobile communication module for accessing the network. In embodiments, the mobile communication module may be accessed to a mobile communication network for each generation such as 2G to 5G mobile communication network.

In embodiments, on receiving a program code, the program code may be executed by the processor 111 and may be stored in a disk drive of the memory unit 113 or in a non-volatile memory of a different type from the disk drive for executing the program code.

In embodiments, the computing device 110 may include a variety of computer-readable medium or media. The computer-readable medium or media may be any available medium or media that are accessible by the computing device 100. For example, the computer-readable medium or media may include, but is not limited to, both volatile and non-volatile media, removable or non-removable media.

In embodiments, the memory unit 113 may store a driver, an application program, data, and a database for operating the apparatus 100 therein. In addition, the memory unit 113 may include a computer-readable medium in a form of a volatile memory such as a random access memory (RAM), a non-volatile memory such as a read only memory (ROM), and a flash memory. For instance, it may be, but is not limited to, a hard disk drive, a solid-state drive, an optical disk drive. In embodiments, each of the memory unit 113 and the storage device 115 may be program modules such as the imaging software 113*b*, 115*b* and the operating systems 113*c*, 115*a* that can be immediately accessed so that a data such as the imaging data 113*a*, 115*c* is operated by the processor 111.

In embodiments, the machine learning model 13 may be installed into at least one of the processor 111, the memory unit 113 and the storage device 115. The machine learning model 13 may be, but is not limited to, at least one of a deep neural network (DNN), a convolutional neural network (CNN) and a recurrent neural network (RNN), which are one of the machine learning algorithms.

The Deep Neural Network (DNN) is an Artificial Neural Network (ANN) composed of multiple hidden layers between the input layer and the output layer. Like a conventional artificial neural network, the DNN can model complex nonlinear relationships. For example, in the structure of the DNN for object recognition, each object can be represented hierarchically as a composition of basic elements in an image. Additional layers can gradually aggregate the features of sublayers. This characteristic of deep neural networks allows them to model complex data with fewer units (nodes) compared to similarly performing artificial neural networks.

The Convolutional Neural Networks (CNNs) are a type of multilayer perceptron designed to require minimal preprocessing. The CNNs consist of one or more convolutional layers followed by conventional artificial neural network layers, with additional utilization of weights and pooling layers. Thanks to this structure, the CNNs can effectively utilize 2D input data. Compared to other deep learning architectures, the CNNs perform well in both image and speech processing fields. The CNNs can also be trained using standard backpropagation, and they are easier to train and use fewer parameters than other feedforward artificial neural network techniques.

In deep learning, Convolutional Deep Belief Networks (CDBNs) have been developed. The CDBNs are structurally similar to traditional CNNs, allowing for effective use of 2D structures while benefiting from pretraining in Deep Belief Networks (DBNs). The CDBNs provide a common structure that can be used in various image and signal processing techniques and have been used in benchmarking results with standard image datasets like CIFAR.

The Recurrent Neural Networks (RNNs) refer to neural networks in which the connections between units form a directed cycle. The RNNs can use internal memory within the network to process arbitrary inputs. Due to this feature, the RNNs are applied in fields such as handwriting recognition and exhibit high recognition rates.

In embodiments, the camera 150 may include an image sensor (not shown) that captures an image of a subject and photoelectrically converts the image into an image signal and may photograph a biometric image of the subject using the image sensor. The photographed biometric image may be stored in the memory unit 113 or the storage device 115 or may be provided to the processor 111 through the input/output interface 117 and processed based on the machine learning model 13.

Figure 3:
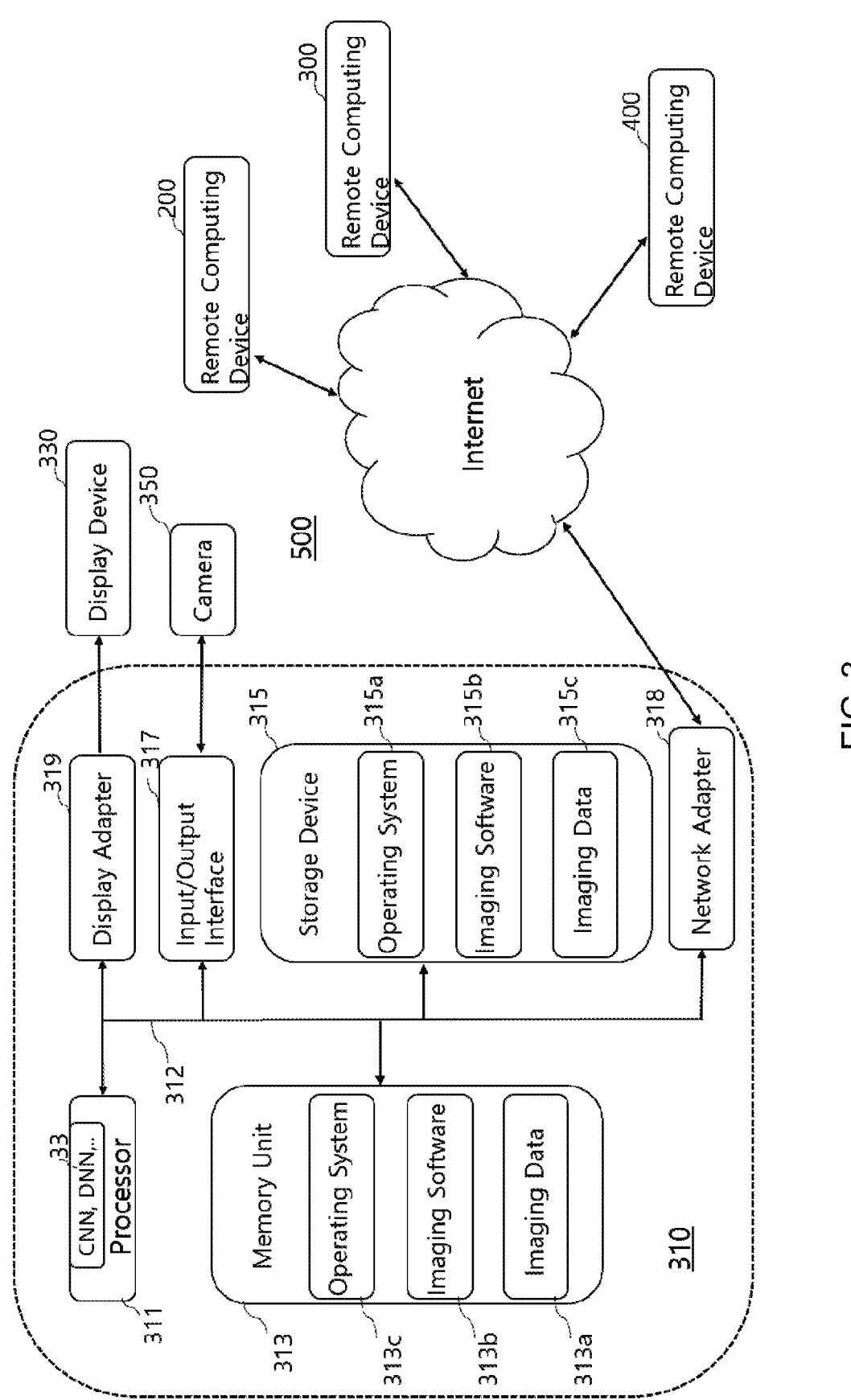
FIG. 3 shows a schematic diagram of an illustrative system for supporting reading of a biometric image according to embodiments of the present disclosure.

FIG. 3 is a schematic diagram of an illustrative system 500 for supporting reading of a biometric image according to embodiments of the present disclosure.

Referring to FIG. 3, the system 500 may include a computing device 310 and one and more remote computing devices 200, 300, 400. In embodiments, the computing device 310 and the remote computing devices 200, 300, 400 may be connected to each other through a network. The components 310, 311, 312, 313, 315, 317, 318, 319, 330 of the system 500 are similar to their counterparts in FIG. 2. In embodiments, each of remote computing devices 200, 300, 400 may be similar to the apparatus 100 in FIG. 2. For instance, each of remote computing devices 200, 300, 400 may include each of the subsystems, including the processor 311, the memory unit 313, an operating system 313*c*, 315*a*, an imaging software 313*b*, 315*b*, an imaging data 313*a*, 315*c*, a network adapter 318, a storage device 315, an input/output interface 317 and a display adapter 319. Each of remote computing devices 200, 300, 400 may further include a display device 330 and a camera 350. In embodiments, the system bus 312 may connect the subsystems to each other.

In embodiments, the computing device 310 and the remote computing devices 200, 300, 400 may be configured to perform one or more of the methods, functions, and/or operations presented herein. Computing devices that implement at least one or more of the methods, functions, and/or operations described herein may comprise an application or applications operating on at least one computing device. The computing device may comprise one or more computers and one or more databases. The computing device may be a single device, a distributed device, a cloud-based computer, or a combination thereof.

It shall be noted that the present disclosure may be implemented in any instruction-execution/computing device or system capable of processing data, including, without limitation laptop computers, desktop computers, and servers. The present invention may also be implemented into other computing devices and systems. Furthermore, aspects of the present invention may be implemented in a wide variety of ways including software (including firmware), hardware, or combinations thereof. For example, the functions to practice various aspects of the present invention may be performed by components that are implemented in a wide variety of ways including discrete logic components, one or more application specific integrated circuits (ASICs), and/or program-controlled processors. It shall be noted that the manner in which these items are implemented is not critical to the present invention.

Figure 4:
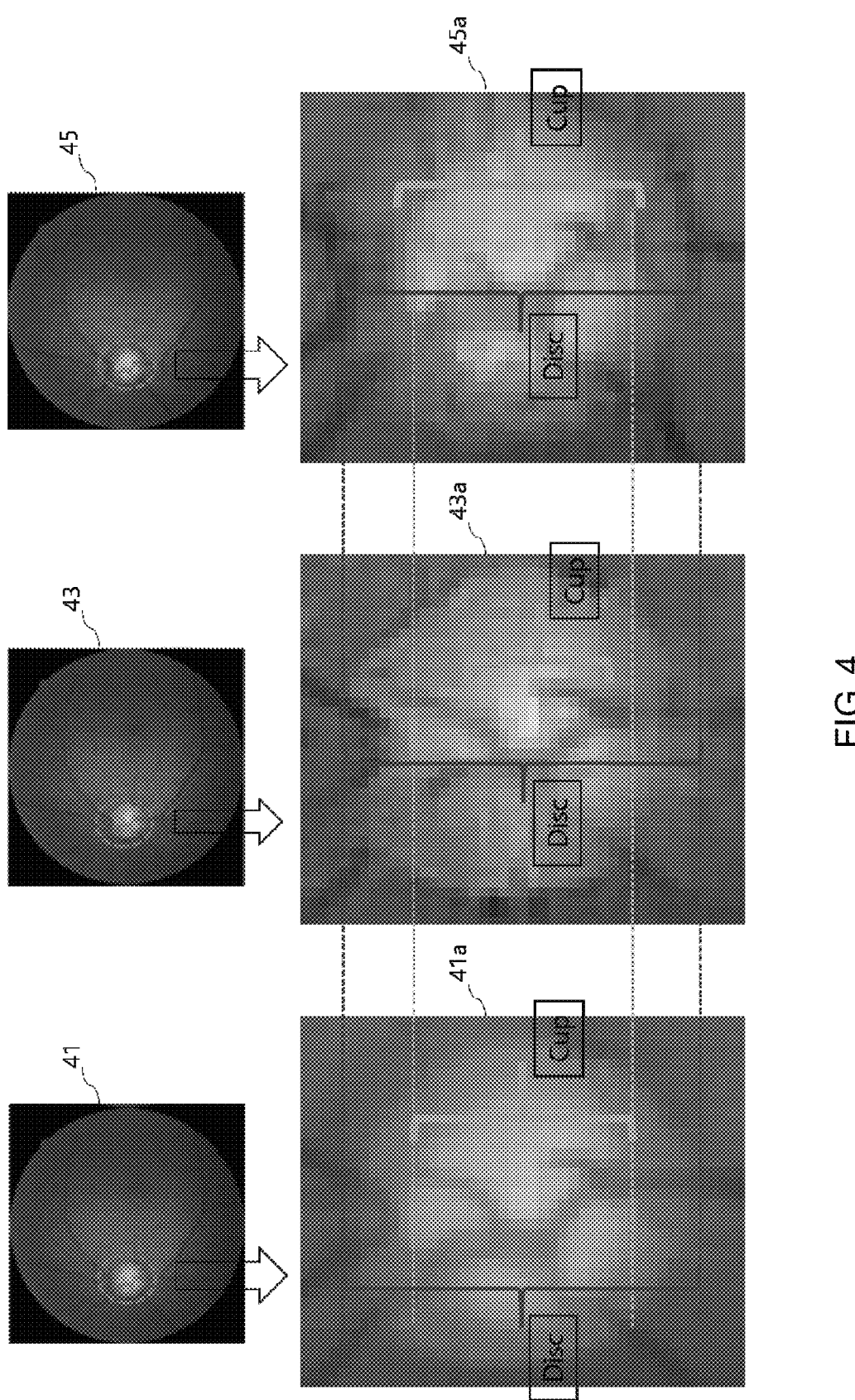
FIG. 4 is a view showing fundus images including a C/D ratio information acquired by an apparatus according to embodiments of the present disclosure.

FIG. 4 is a view showing fundus images including a C/D ratio information acquired by an apparatus 100 according to embodiments of the present disclosure.

As an example of biometric images, the fundus image is an image that can detect conditions such as glaucoma in the subject's eyes and can provide information for predicting conditions like cardiovascular diseases through the abnormalities observed in the fundus image. A value of the C/D ratio is defined as the value of the maximum distance of an area corresponding to a cup in the fundus image divided by the maximum distance of an area corresponding to a disc in a fundus image. Typically, the value of the C/D ratio may be a measure of predicting a disease such as glaucoma in the fundus image.

Referring to FIG. 4, a first fundus image 41 is obtained from the subject based on the machine learning model 13 of the apparatus 100 in FIG. 1, and an enlarged first image 41a is obtained by enlarging a cup and disc area in the first fundus image 41. A second fundus image 43 is obtained by mapping a negative adversarial factor to the cup and disc area of the first fundus image 41, the negative adversarial factor means an adversarial factor to make the prediction value converge to the set value 0 as mapping method by the processor 111 in described conjunction with FIG. 1. That is, the second fundus image 43 is an image with the C/D ratio in the normal range that cannot diagnose any disease based on the machine learning model, and an enlarged second image 43a is obtained by enlarging the cup and disc area in the second fundus image 43. A third fundus image 45 is obtained by mapping a positive adversarial factor to the cup and disc area of the first fundus image 41, the positive adversarial factor means an adversarial factor to make the prediction value converge to the set value 1 as mapping method by the processor 111 described in conjunction with FIG. 1. Namely, the third fundus image 45 is an image with the C/D ratio in the abnormal range that can diagnose any disease based on the machine learning model, and an enlarged third image 45a is obtained by enlarging the cup and disc area in the third fundus image 45. The enlarged first, second, third images 41a, 43a, 45a may be generated by the processor 111 processing each of the first, second, third fundus images 41, 43, 45. In this case, the first feature information of the first fundus image 41 shows the value of the C/D ratio, and the second feature information of the second fundus image 43 and the third feature information of the third fundus image 45 show the values of the C/D ratio changed by mapping the adversarial factor to the first fundus image 41. The method of mapping the adversarial factor may be similar to mapping described in FIG. 1.

More specifically, the first fundus image 41 obtained based on the machine learning model 13 is a fundus image that can show the findings (a practitioner's opinion) in which it appears any disease such as glaucoma. However, on reading the first fundus image 41, the accuracy or reliability of such findings on the first fundus image 41 may be poor.

In embodiments, the processor 111 may generate the second fundus image 43 so that the value of the C/D ratio is close to the normal range of the fundus image, or the third fundus image 45 so that the value of the C/D ratio is close to the abnormal range of the fundus image. The second and third fundus images 43, 45 may be displayed on the display device 130 so that the entity can compare the first fundus image 41 with the second and third fundus images 43, 45. In alternative embodiments, the enlarged first, second, third image 41a, 43a, 45a generated by the processor 111 may be displayed on the display device 130 so that the entity can compare the enlarged first image 41a with the enlarged second and third images 43a, 45a. Since the apparatus 100 can allow the entity to compare the first fundus image with the second fundus image or the third fundus image when reading the fundus image, the reliability and accuracy of a reading (e.g., a finding, a prediction, a diagnosis) on the first fundus image by the apparatus 100 can be improved. Thus, the apparatus 100 can allow the entity to explain the reason why such the reading was obtained.

Figure 5:
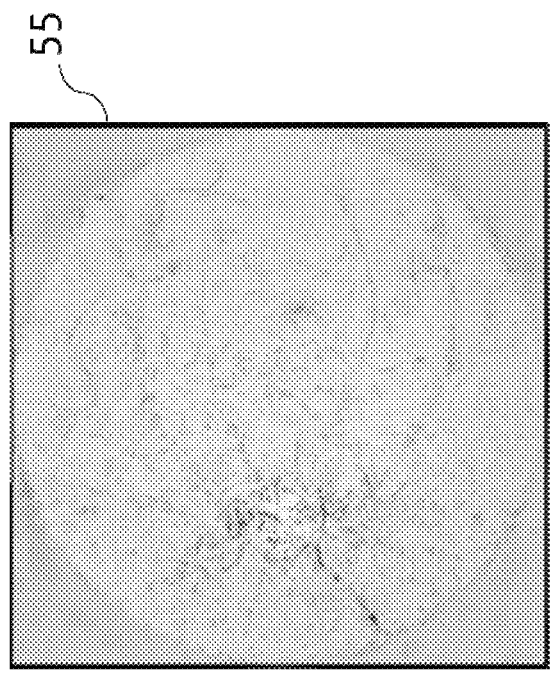
FIG. 5 is a view showing images obtained by filtering fundus images of FIG. 4 by an apparatus according to embodiments of the present disclosure.
Figure 5:
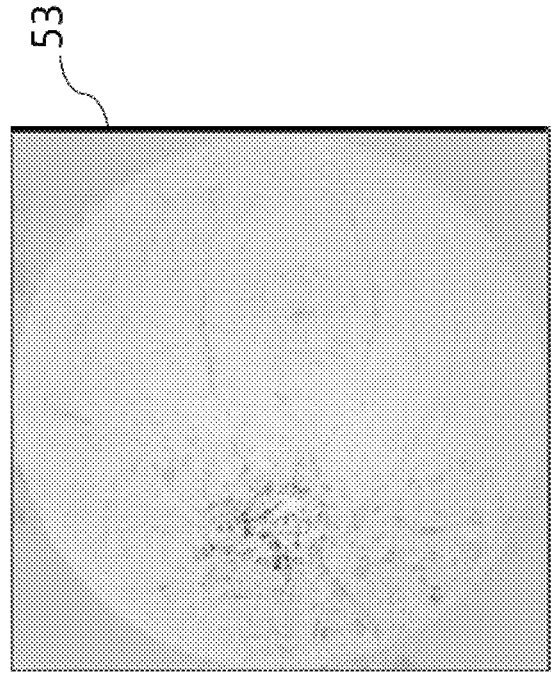

FIG. 5 is a view showing images obtained by filtering a second fundus image 43 and a third fundus image 45 in FIG. 4 using the processor 111 of the apparatus 100 according to embodiments of the present disclosure.

Referring to FIG. 5, a first image 53 and second image 55 correspond with the second fundus image 43 and the third fundus image 45 in FIG. 4, respectively. The first image 53 and second image 55 are images visualizing the adversarial noise mapped to each of the second fundus image 43 and the third fundus image 45. The visualized images 53, 55 may be generated by filtering each of the second fundus image 43 and the third fundus image 45 having the adversarial noise using an image filter such as a high pass filter. The image filter may be executed by the processor 111 accordingly to the present disclosure. The visualized images 53, 55 may be provided to the entity so that the entity can compare the visualized images 53, 55 to each other.

It is shown that the adversarial noise such as a dot is mapped around a disc area where the C/D ratio information can be found in the fundus image. More specifically, the first image 53 shows that the adversarial noise is more intensively mapped to the disc area, as an image with the value of the C/D ratio in the normal range. The second image 55 shows that the adversarial noise is mapped not only to the disc area but also to the entire area of the fundus image, as an image with the value of the C/D ratio in the abnormal range.

Thus, the apparatus 100 may visualize the adversarial noise of the fundus image so that the entity knows the feature information in which the C/D ratio is changing at a certain position in the fundus image. Therefore, the apparatus 100 may allow the entity to read the fundus image with more the accuracy and reliability.

Figure 6:
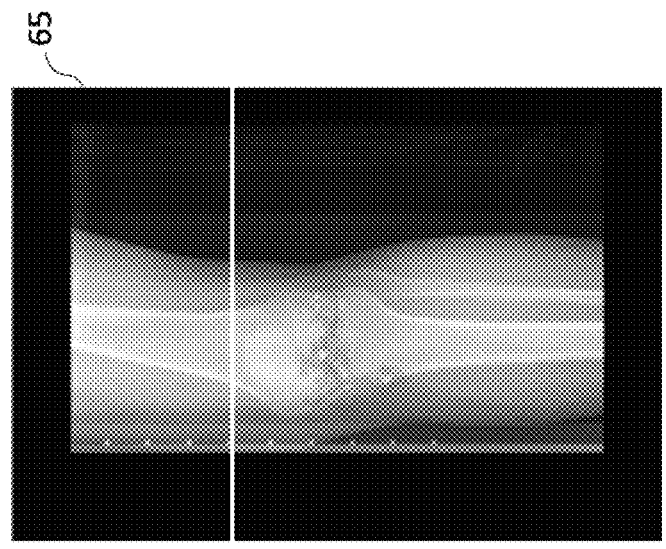
FIG. 6 is a view showing a bone joint image including joint spacing information acquired by an apparatus according to embodiments of the present disclosure.
Figure 6:
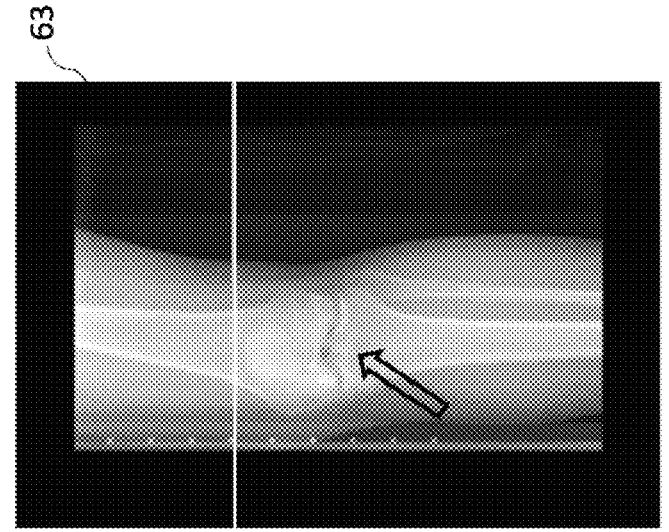
Figure 6:
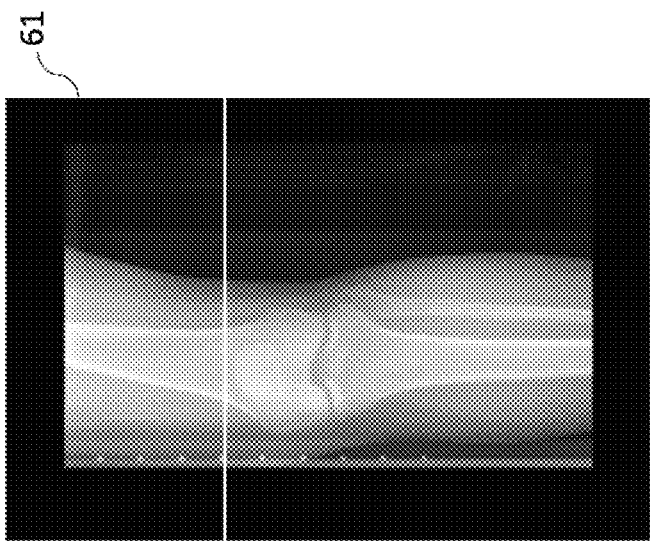

FIG. 6 is a view showing a bone joint image including joint spacing information acquired by an apparatus according to embodiments of the present disclosure.

As an example of a biometric image, a bone joint image is an image that can confirm the type of arthritis in the joints of a subject. The gap information between joints in the bone joint image is a scale for predicting arthritis.

Referring to FIG. 6, the first joint image 61 is an image generated by mapping a negative adversarial factor to joint images (not shown) obtained from the subject based on a machine learning model of the apparatus 100 according to embodiments of the present disclosure. Here, the negative adversarial factor means an adversarial factor to make the prediction value converge to the set value 0 as mapping method by the processor 111 in described conjunction with FIG. 1. In other words, the first joint image 61 is an image with a normal range of joint gaps that cannot diagnose any diseases based on the machine learning model. The second joint image 63 is an image generated by mapping a positive adversarial factor to joint images (not shown) obtained from the subject based on a machine learning model of the apparatus 100 according to embodiments of the present disclosure. Here, the positive adversarial factor means an adversarial factor to make the prediction value converge to the set value 1 as mapping method by the processor 111 in described conjunction with FIG. 1. That is, the second joint image 63 is an image with an abnormal range of joint gaps that can diagnose various diseases (e.g., arthritis) based on the machine learning model, as shown in the arrow-indicated portion.

The third joint image 65 is an image that visualizes adversarial noise mapped by overlaying the first joint image 61 and the second joint image 63.

Mapping adversarial noise to joint images, as stated above, can be performed by processors 111 311 and joint images newly created by overlaying joint images can also be performed by processors 111, 311. Furthermore, these newly created joint images can be displayed on display devices 130, 330, allowing entities to have a means to read bone joint images with higher reliability.

Figure 7:
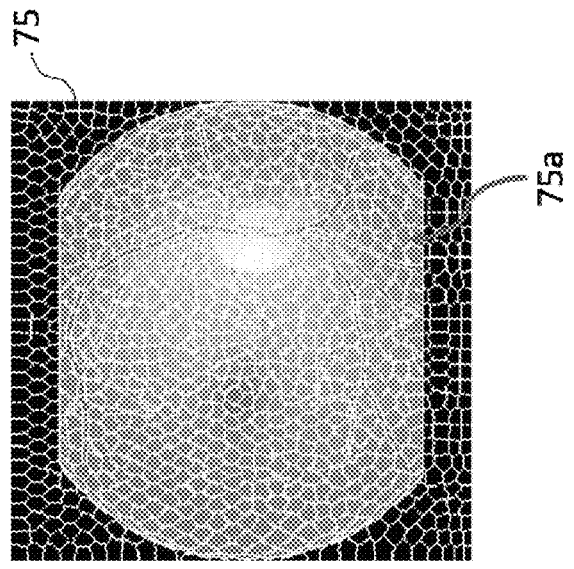
FIG. 7 is a view conceptually showing an image in which an apparatus according to embodiments of the present disclosure spatially maps adversarial noise.
Figure 7:
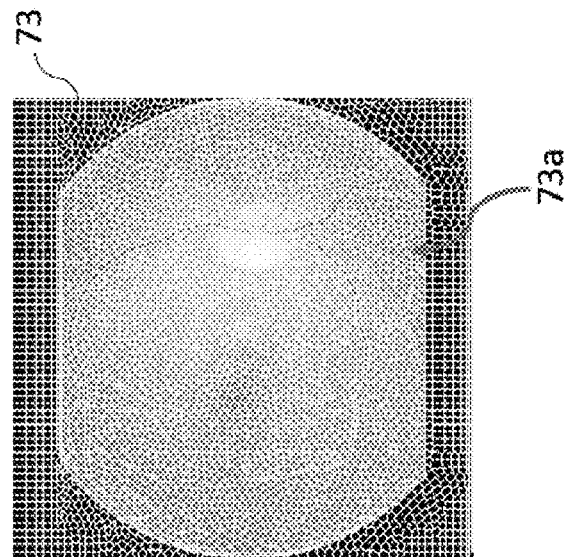
Figure 7:
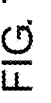
Figure 7:
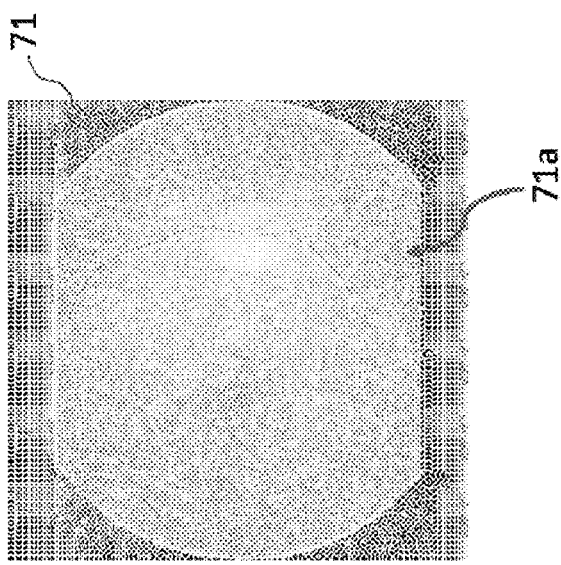

FIG. 7 is a view conceptually showing an image in which an apparatus according to embodiments of the present disclosure spatially maps adversarial noise.

As depicted, the first image 71 represents pixels 71a that make up the image spatially segmented, and when the processor 111 maps the first image 71, it can map adversarial noise on the first image by pixel. The second image 73 represents unit cells 73a segmented spatially by grouping pixels that make up the second image 73. When the processor 111 maps the second image 73, it can map adversarial noise by unit cell. Furthermore, the third image 75 represents group cells 75a segmented spatially by grouping unit cells that make up the third image 75. When the processor 111 maps the third image 75, it can map adversarial noise by group cell. In this case, grouping of pixels can be grouped into unit cells by grouping neighboring pixels, and grouping of unit cells can be grouped into group cells by grouping neighboring unit cells.

In this way, mapping adversarial noise at the pixel, unit cell, and group cell levels can reduce a load for computing the device 100 for a noise mapping and increase the realism of the image resulting from noise mapping.

Figure 8A:
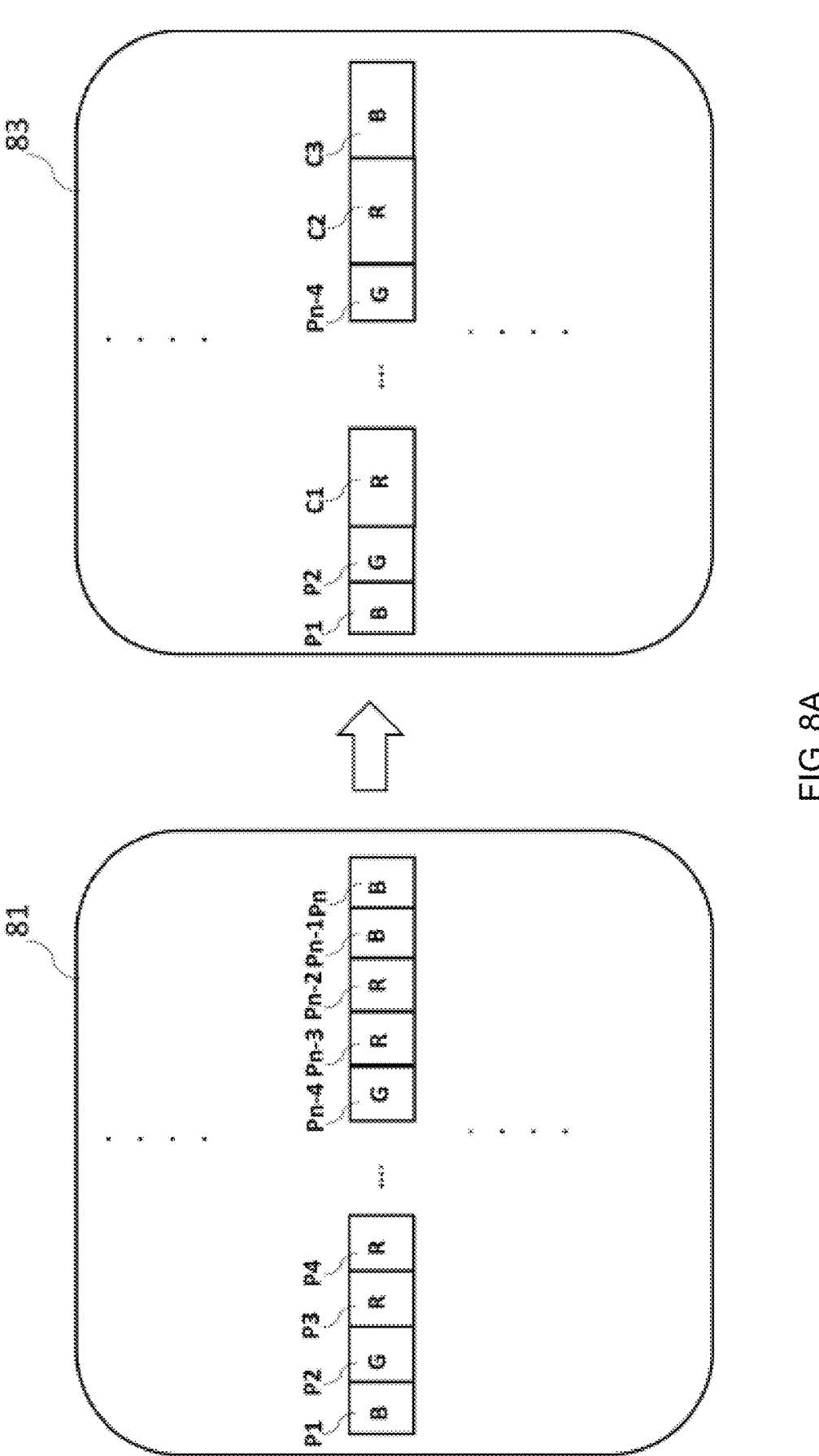
FIGS. 8A and 8B are schematic diagrams illustrating a process grouping pixels of an image for mapping adversarial noise, according to an embodiment of the present disclosure.
Figure 8B:
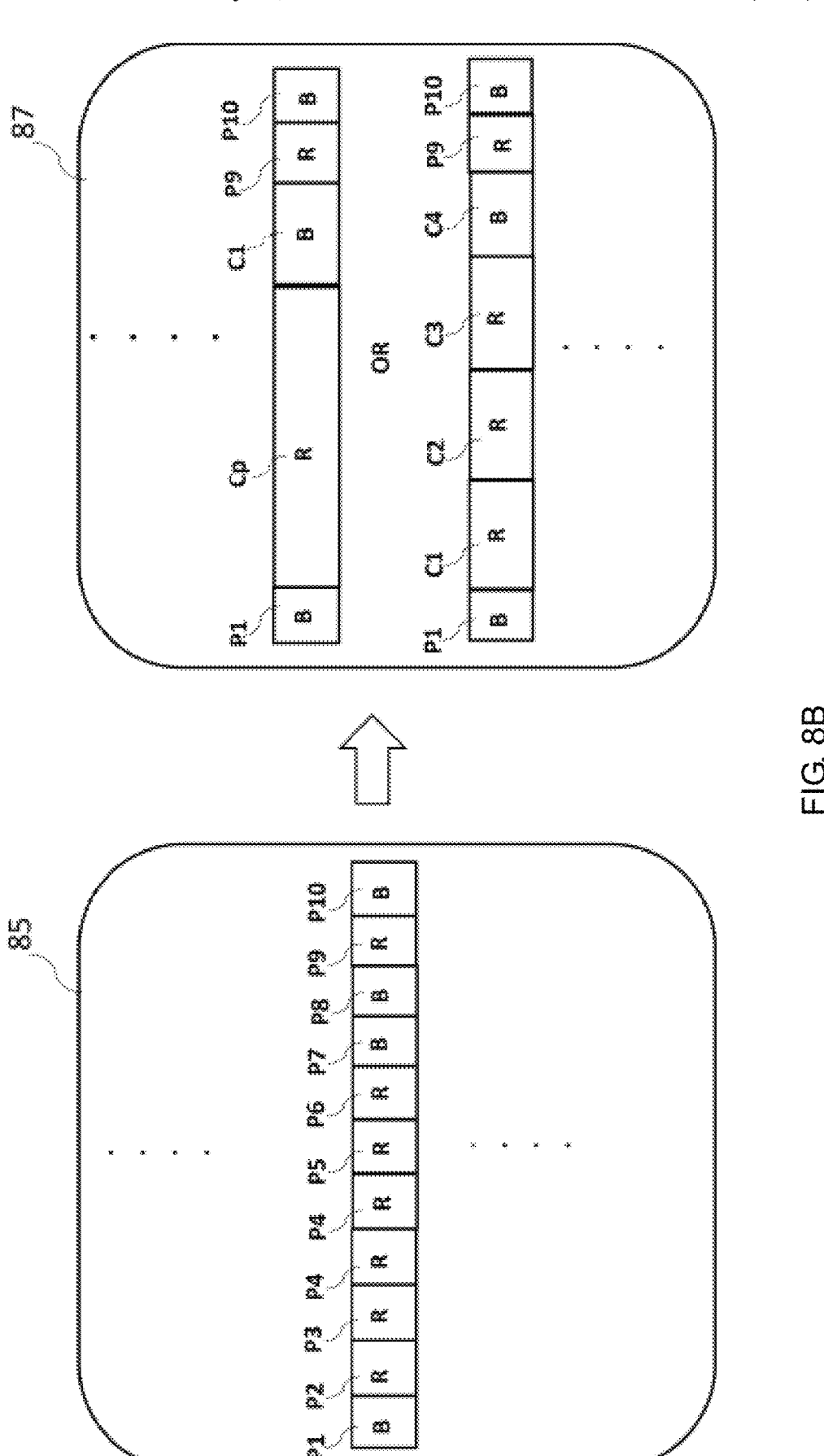

FIGS. 8A and 8B are schematic diagrams illustrating a process grouping pixels of an image for mapping adversarial noise, according to an embodiment of the present disclosure.

FIG. 8A illustrates an embodiment of grouping the pixels, where the first diagram 81 represents pixels before grouping the pixels, and the second diagram 83 represents pixels (P1, P2, . . . . Pn–4) and unit cells (C1, C2, C3) shown after grouping any pixels. The pixels (P1, P2, P3, . . . , Pn) representing an image may be grouped with adjacent pixels according to the color of the pixel to form one unit cell (C1, C2, C3). For example, if the third pixel (P3) and the fourth pixel (P4) adjacent to the third pixel (P3) have the same color (R), the third pixel (P3) and the fourth pixel (P4) are grouped into one unit cell (C1). Additionally, the unit cell may be formed by grouping adjacent pixels based on various criteria, not limited to grayscale or brightness. Although not shown in the drawings, unit cells grouped by the pixel may be grouped into group cells by grouping adjacent unit cells using the aforementioned grouping method.

FIG. 8B illustrates an another embodiment of grouping the pixels, where the first diagram 85 represents pixels before grouping the pixels, and the second diagram 87 represents pixels (P1, P9, P10) and unit cells (C1, C2, C3, C4, Cp) shown after grouping any pixels. When the colors of adjacent pixels (P1, P2, P3, . . . , P10) representing the image are continuously the same, adjacent pixels can be grouped into a single unit group cell (Cp). For example, if the second pixel (P2) to the sixth pixel (P6) have the same color (R), they can be grouped into a single unit group cell (Cp). However, when mapping adversarial noise to a single unit group cell, even if the colors of adjacent pixels (P2, P3, P4, P5, P6) are continuously the same, the unit cells (C1, C2, C3) may be grouped by limiting the distance between adjacent pixels (P2, P3, P4, P5, P6) to prevent the visual effect of the image from being deteriorated due to the mapping. Furthermore, if the gray scale or brightness of adjacent pixels is continuously the same, the unit cells may be, but is not limited to be grouped in the same manner as above. Additionally, if at least one of color, gradation, and brightness of the unit cell grouped at the pixel level is same to that of adjacent unit cell, a group cell may be formed by grouping with adjacent unit cells.

Figure 9A:
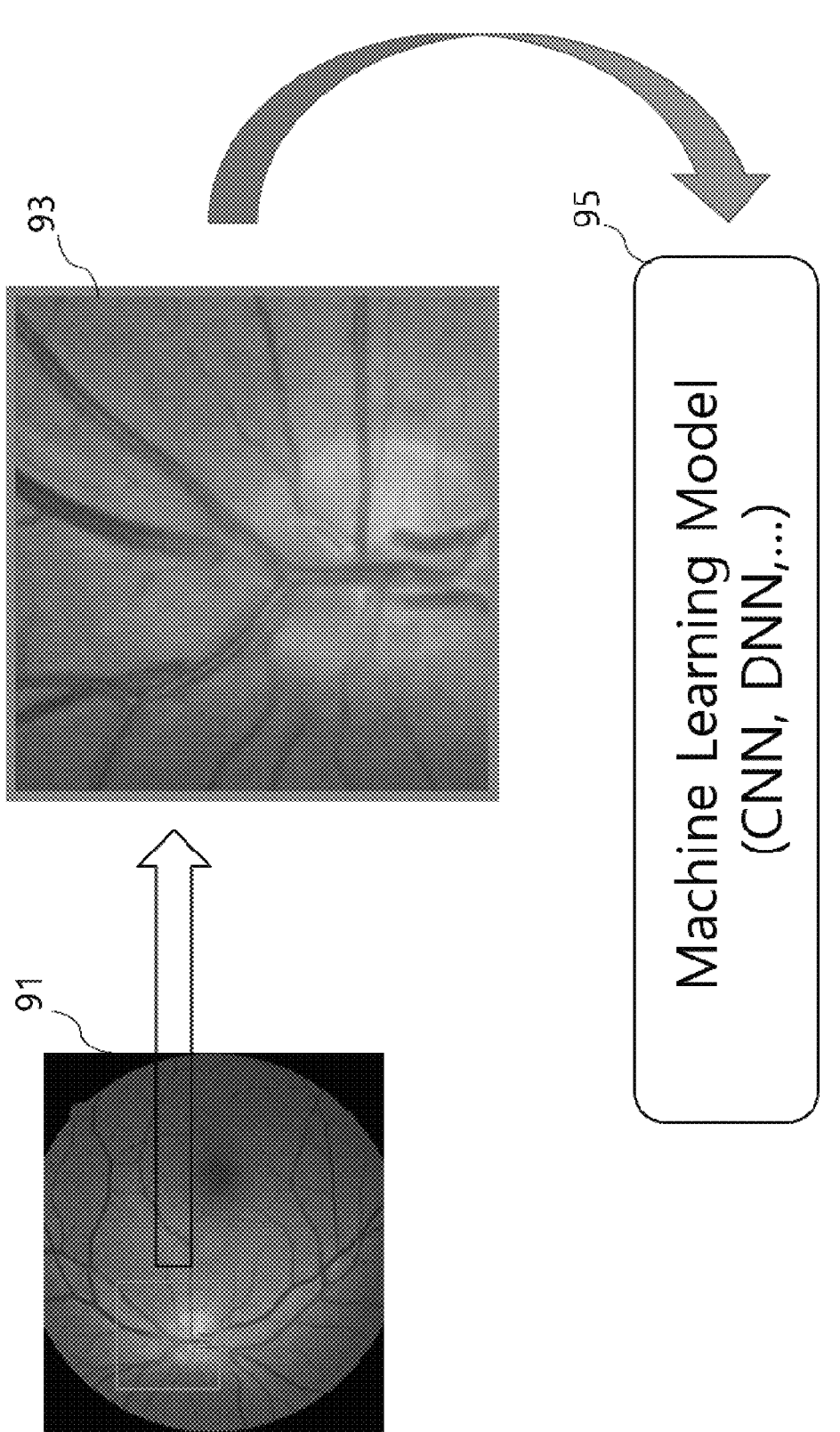
FIGS. 9A and 9B are a view showing an illustrative process for generating a pre-biometric image by apparatus according to embodiments of the present disclosure.
Figure 9B:
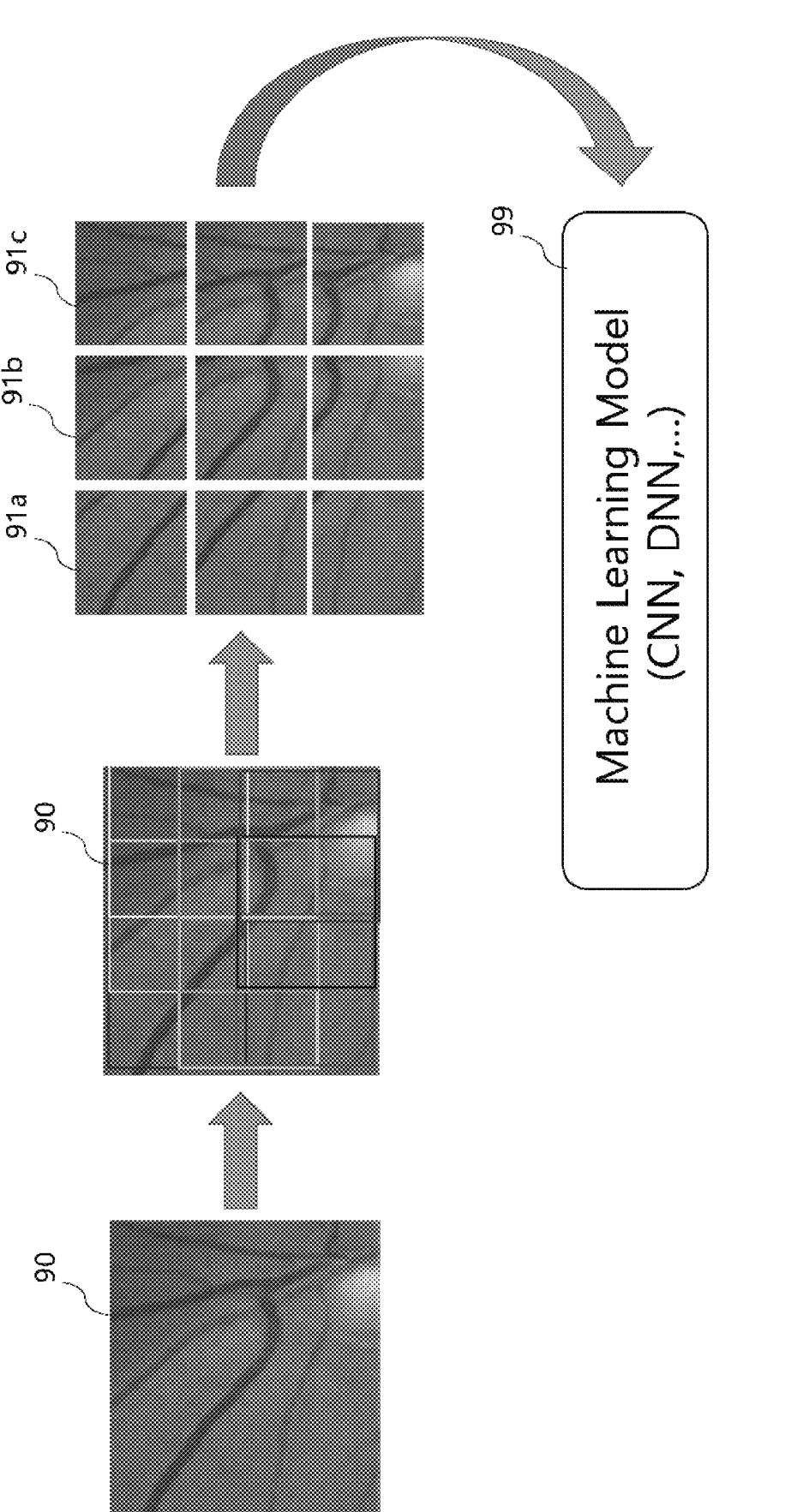

FIGS. 9A and 9B are a view showing an illustrative process for generating a pre-biometric image by apparatus according to embodiments of the present disclosure. In embodiments, an example of a biometric image depicted in FIGS. 9A and 9B is a fundus image.

As depicted in FIG. 9A, Initially, an original fundus image 91 of the subject may be obtained by taking an image by a camera (not shown). After that, pre-fundus image 93 may be generated by pre-processing the original fundus image 91 by the processor 111 in FIG. 1 so that a specific region of the original fundus image is enlarged in order to more intensively check a feature information on the original fundus image 91. In this case, the specific region may be, but is not limited to, the optic nerve papilla region including retinal blood vessels. Finally, The pre-fundus image 93 may be input to the machine learning model 95, and the fundus disease may be predicted by extracting the feature information from the pre-fundus image 93 based on the machine learning model 95.

As depicted in FIG. 9B, First, an enlarged fundus image 90 may be obtained by pre-processing an image like the original fundus image 91 described in FIG. 9A. The pre-processing may be executed by the processor 111 in FIG. 1. After that, the enlarged fundus image 90 may be partially partitioned by a plurality of areas. In this case, each of the plurality of areas may have the same size or different sizes. Each of the plurality of areas may overlap each other locally. At that, a plurality of pre-fundus images 91a, 91b, 91c may be generated according to the partitioned areas. Finally, each of the plurality of pre-fundus images 91a, 91b, 91c may be input to the machine learning model 99 and the fundus disease may be predicted by extracting the feature information from each of the pre-fundus images 91a, 91b, 91c based on the machine learning model 99.

The pre-fundus image may be generated in various ways. For example, the pre-fundus image may be generated by rotating around a reference axis of the original fundus image, or/and the pre-fundus image may be generated by adjusting the contrast or brightness of the original fundus image or/and by flipping around a horizontal or vertical axis of the original fundus image. Thus, if the pre-fundus image inputs the machine learning model, thereby more improving an accuracy of prediction of the fundus disease.

FIG. 10 shows a flowchart illustrating an exemplary process for supporting reading of a biometric image by a processor 111 according to embodiments of the present disclosure.

Referring to FIG. 10, at step S910, the processor 111 may obtain a first biometric image of a subject from a fundus camera and extract a first feature information from the first biometric image of the subject. In embodiments, the first biometric image may be stored in the memory unit 113, 313 or the storage device 115, 315 included to the computing device 110, 310 (as discussed in conjunction with FIGS. 2 and 3). At step S920, the processor 111 may map an adversarial factor (i.e., the adversarial noise) to the first biometric image to change the first feature information of the first biometric image, thereby generating a second biometric image with a second feature information. Mapping the adversarial factor may be similar to mapping described in FIG. 1. In embodiments, the processor 111 may generate images in which a specific area of the first biometric image and the second fundus image is enlarged. In embodiments, the processor 111 may generate a third biometric image in which an adversarial noise is visualized, by filtering the second biometric image using an image filter. In alternative embodiments, the processor 111 may generate a pre-first biometric image by pre-processing the first biometric image so that a specific area of the first biometric image is enlarged or partially partitioned. At step S930, the processor 111 may display the biometric image having the first feature information and the second biometric image having the second feature information on a display device so as to provide an entity with the first and second feature information. In embodiments, the processor 111 may display at least one of the enlarged images and the visualized third biometric image on the display device.

As such, the apparatus and method for supporting reading of a biometric image according to embodiments of the present disclosure is capable of explaining the reason for biometric image reading based on the machine learning model and enabling entities to read the biometric image with greater reliability.

Embodiments of the present invention may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present disclosure may further relate to computer products with a non-transitory, tangible computer-readable medium that have computer code thereon for performing various computer-implemented operations. The media and computer code may be those specially designed and constructed for the purposes of the present disclosure, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. One skilled in the art will recognize no computing system or programming language is critical to the practice of the present disclosure. One skilled in the art will also recognize that a number of the elements described above may be physically and/or functionally separated into sub-modules or combined together.

Embodiments of the present disclosure may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

It will be appreciated to those skilled in the art that the preceding examples and embodiment are exemplary and not limiting to the scope of the present invention. It is intended that all permutations, enhancements, equivalents, combinations, and improvements thereto that are apparent to those skilled in the art upon a reading of the specification and a study of the drawings are included within the true spirit and scope of the present invention.

The invention claimed is:

1. An apparatus for supporting reading of a biometric image of a subject, comprising:

a processor; and a memory including one or more sequences of instructions which, when executed by the processor, causes steps to be performed comprising:

extracting a first feature information from a first biometric image of the subject based on a machine learning model;

generating a second biometric image having a second feature information by mapping an adversarial noise to the first biometric image so that the first feature information of the first biometric image is changed;

generating a third biometric image in which the adversarial noise is visualized, by filtering the second biometric image mapped by the adversarial noise therein; and displaying the first biometric image having the first feature information, the second biometric image having the second feature information and the third biometric image on a display device.

2. The apparatus of claim 1, wherein the steps further comprises:

generating images in which a specific area of each of the first biometric image and the second biometric image is enlarged; and displaying the images on the display device.

3. The apparatus of claim 1, wherein the steps further comprises:

generating a pre-biometric image by pre-processing the first biometric image to enlarge or partially partition a specific area of the first biometric image.

4. The apparatus of claim 1, wherein the adversarial noise comprises at least one of gradation levels of R, G, and B pixels of the first biometric image, a color of R, G, and B pixels of the first biometric image, and a contrast ratio of the first biometric image.

5. The apparatus of claim 1,
wherein the second biometric image is generated by repeatedly mapping by the adversarial noise to the first biometric image at least one or more times so that a prediction value of the first feature information obtained based on the machine learning model for the first biometric image converges to a set value.

6. The apparatus of claim 5,
wherein the number of second biometric image is dependent on the number of the set value.

7. The apparatus of claim 1,
wherein the first feature information is extracted by utilizing a clinical information of the subject.

8. The apparatus of claim 1,
wherein the first biometric image includes a fundus image, a first feature information of the fundus image comprises at least one of a cup-to-disk ratio, a thickness change for a disc rim thinning, a contrast for a retinal nerve fiber layer defect and, a location of a retinal hemorrhage included in the fundus image.

9. The apparatus of claim 1,
wherein the adversarial noise is mapped into the first biometric image in an unit of grouped cells, which spatially group image pixels composing the first biometric image.

10. The apparatus of claim 9,
wherein the image pixels are grouped based on a color of an adjacent image pixels each other.

11. A method for supporting reading of a biometric image of a subject, comprising:
extracting a first feature information from a first biometric image of the subject based on a machine learning model;
generating a second biometric image having a second feature information by mapping an adversarial noise to the first biometric image so that the first feature information of the first biometric image is changed;
generating a third biometric image in which the adversarial noise is visualized, by filtering the second biometric image mapped by the adversarial noise therein; and
displaying the first biometric image having the first feature information, the second biometric image having the second feature information and the third biometric image on a display device.

12. The method of claim 11, further comprising:
generating images in which a specific area of each of the first biometric image and the second biometric image is enlarged; and
displaying the images on the display device.

13. The method of claim 11, further comprising:
generating a pre-biometric image by pre-processing the first biometric image so that a specific area of the first biometric image is enlarged or partially partitioned.

* * * * *